（12） United States Patent
Green

(10) Patent No.: US 7,831,014 B2
(45) Date of Patent: Nov. 9, 2010

(54) BREAST TREATMENT MACHINE

(75) Inventor: Michael C. Green, Palo Alto, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 375 days.

(21) Appl. No.: 12/105,795

(22) Filed: Apr. 18, 2008

(65) Prior Publication Data

US 2009/0264968 A1    Oct. 22, 2009

(51) Int. Cl.
*A61B 6/04* (2006.01)
*H05G 1/00* (2006.01)
(52) U.S. Cl. .................................. 378/37; 378/208
(58) Field of Classification Search .............. 378/4, 378/19, 37, 20, 63, 64, 65, 68, 208; 600/407; 607/88
See application file for complete search history.

(56) References Cited

U.S. PATENT DOCUMENTS

| | | | |
|---|---|---|---|
| 6,298,114 B1 * | 10/2001 | Yoda ........................... | 378/37 |
| 7,492,858 B2 * | 2/2009 | Partain et al. ................. | 378/37 |
| 7,597,104 B2 * | 10/2009 | Zheng et al. ................. | 128/869 |
| 2007/0092059 A1 * | 4/2007 | Eberhard et al. ............. | 378/37 |
| 2008/0230074 A1 | 9/2008 | Zheng et al. | |
| 2008/0298536 A1 * | 12/2008 | Ein-Gal ........................ | 378/4 |

FOREIGN PATENT DOCUMENTS

WO    WO2006119426 A2    11/2006

OTHER PUBLICATIONS

Formenti et al., "Prone Accelerated Partial Breast Irradiation after Breast-Conserving Surgery: Preliminary Clinical Results and Dose-Volume Histogram Analysis," Int. J. Radiation Oncology Biol. Phys., Apr. 2004, vol. 60, No. 2, pp. 493-504.
Formenti et al., "Phase I-II Trial of Prone Accelerated Intensity Modulated Radiation Therapy to the Breast to Optimally Spare Normal Tissue," Journal of Clinical Oncology, Jun. 1, 2007, vol. 25, No. 16, pp. 2236-2242.

* cited by examiner

*Primary Examiner*—Irakli Kiknadze
(74) *Attorney, Agent, or Firm*—Houst Consulting

(57) ABSTRACT

An apparatus for irradiating a breast of a patient includes a radiation source, a structure adapted to hold a breast of a patient in receiving a radiation from the radiation source, and a vacuum source. The structure includes a member having an interior generally conformal to a shape of the patient's breast when the breast is uncompressed or pendulous. The vacuum source is adapted to provide a negative pressure in the interior of the member, whereby in use of the apparatus with the patient in a supine position, the breast is held in the generally uncompressed shape. A method of irradiating a breast of a patient includes the steps of placing a breast of a patient in a structure which includes a member having an interior generally conformal to a shape of the patient's breast when pendulous or uncompressed, applying a negative pressure in the interior, thereby bringing the breast in contact with the member in the generally uncompressed shape, and delivering a radiation beam to the breast of the patient in a supine position.

24 Claims, 1 Drawing Sheet

BREAST TREATMENT MACHINE

TECHNICAL FIELD

This invention relates in general to radiation treatment of diseases and in particular radiation apparatus and methods useful in diagnosis and treatment of breast cancer.

BACKGROUND

Breast cancer is the most common cancer among women in the United States except skin cancer. It is estimated that each year, approximately 200,000 American women are diagnosed to have breast cancer. Depending on the type, stage of the cancer and other factors, patients having breast cancer may be treated with surgery, radiation, and other therapies. Surgery involves removal of breast lumps (lumpectomy) or all of the breast tissue (mastectomy). Radiation therapy uses high-energy radiation such as X-rays to kill cancer cells. Most patients receive radiation therapy after lumpectomy. The radiation destroys breast cancer cells that may remain in the area after the lumpectomy. Some patients have radiation therapy before surgery to destroy cancer cells and shrink the tumor.

In radiation therapy of breast cancer, accurate positioning and stabilizing of the breast is important to deliver a radiation dose to a treatment volume. Accurate positioning is particularly necessary during delivery of a boost dose to avoid a skin overdose and/or insufficient radiation dose to portions of the planned treatment volume. Breast tissue is pliable and readily deformable. Repeatable positioning of the breast presents difficulty. Maintaining a stable breast position during a single fraction often presents challenges.

The vast majority of radiation treatment of breast cancer is carried out with the patient in a supine position because of the ease of access and patient comfort. In this position, gravity depresses the breast towards the patient's torso and the breast tends to spread laterally over the chest wall. This makes accurate positioning of the breast more difficult and complicates the location of internal structures for boost dose. Treatment planning options are constrained by the greater proximity of the breast to the chest wall.

Experiments are being conducted in which the radiation treatment is carried out with the patient in a prone position, so that gravity pulls the breast away from the chest wall. This approach simplifies treatment planning while minimizing the radiation dose to the chest wall and lungs. However, in the prone treatment position gravity pulls the heart downward against the anterior chest wall which somewhat counters the benefit of gravity moving the pendulous breast away from the chest wall. Further, patient discomfort and access of the treatment beam to the breast present difficulties with current prone treatment configurations.

SUMMARY

An apparatus for irradiating a breast of a patient is provided comprising a radiation source, a structure adapted to hold a breast of a patient in receiving a radiation from the radiation source, and vacuum source. The structure comprises a member having an interior generally conformal to a shape of the patient's breast when the breast is uncompressed or pendulous. The vacuum source is adapted to provide a negative pressure in the interior of the member, whereby in use of the apparatus with the patient in a supine position the breast is held in the generally uncompressed shape. As used herein, the term "uncompressed body portion" or "uncompressed breast" refers to a body portion or breast that is not compressed or squeezed in a manner that deforms the body portion or breast in its natural or pendulous condition. By way of example, a patient's breast is compressed when the patient is in a supine position and the gravity depresses the breast towards the patient's chest wall. A patient's breast is uncompressed when the patient is in a prone position and the breast is in its natural or pendulous condition.

The member may have a generally hemispherical interior and exterior, thereby a substantially constant wall thickness. The member may also have a generally hemispherical interior and a generally cylindrical exterior, thereby a substantially different wall thickness. In such embodiment, the member is preferably constructed with a material that has an average beam absorption and/or scattering properties substantially same as that of the breast tissue, whereby the effective length of the member-breast material that is traversed by the radiation beam at the nipple end of the breast is about the same as the effective length that is close to the chest wall.

In some embodiments, the structure further comprises an extension coupled to a periphery of the member adapted to hold the tissue between the breast and the axilla. The structure may also include one or more markers adapted to track motions of the breast.

In one aspect, a structure for holding a portion of a body is provided. The structure includes a member having an interior that is generally conformal to a shape of the body portion when pendulous or uncompressed. The member has one or more openings to be connected to a vacuum source which is adapted to provide a negative pressure to the interior, whereby when in use of the structure the body portion is held in the generally uncompressed shape.

The structure may have a generally hemispherical interior and exterior, thereby a substantially constant wall thickness. The structure may also have a generally hemispherical interior and a generally cylindrical exterior, thereby a substantially different wall thickness. In such embodiment, the member is preferably constructed with a material that has an average radiation beam absorption and/or scattering properties substantially same as that of the body portion.

The structure can be adapted to hold a breast of a patient in a supine position for radiation therapy of breast cancer. As such, the structure may further comprise an extension coupled to the member adapted to hold tissue between the breast and axilla.

In another aspect, a method of irradiating a breast of a patient is provided. The method comprises the steps of placing a breast of a patient in a structure which includes a member having an interior generally conformal to a shape of the patient's breast when pendulous or uncompressed, applying a negative pressure in the interior, thereby the breast is brought in contact with the member in the generally uncompressed shape, and delivering a radiation beam to the breast of the patient in a supine position. By way of example, the radiation beam is X-ray beam at a mega-volt level.

BRIEF DESCRIPTION OF THE DRAWINGS

These and various other features and advantages of the present invention will become better understood upon reading of the following detailed description in conjunction with the accompanying drawings and the appended claims provided below, where:

DETAILED DESCRIPTION OF VARIOUS EMBODIMENTS

Figure 1:
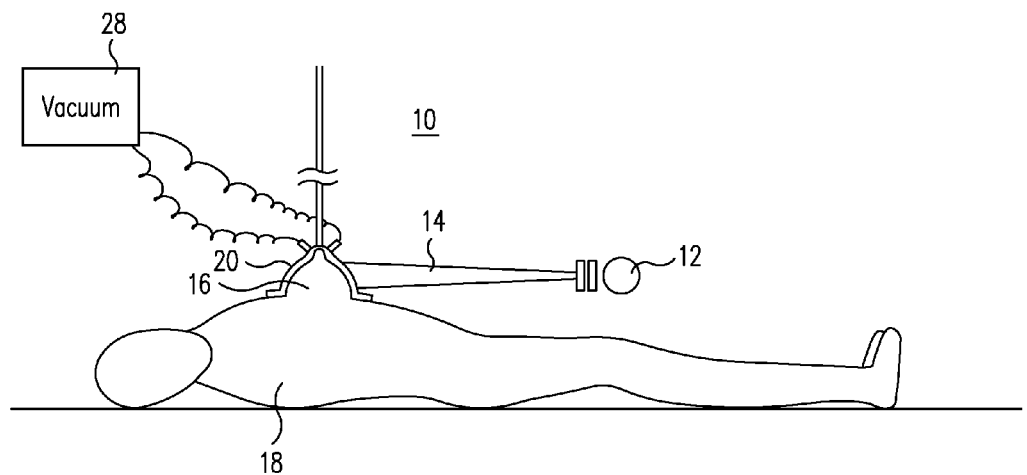
FIG. 1 is a schematic diagram illustrating a radiation apparatus in accordance with one embodiment of the invention.

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention. For instance, various embodiments of the invention are described with human breasts for illustration purpose. It will be appreciated that the claimed invention can also be used in animals, and other human body parts.

FIG. 1 illustrates a radiation apparatus 10 in accordance with some embodiments of the invention. The apparatus 10 comprises a radiation source 12 adapted to generate a radiation beam 14 to a portion 16 of a body 18 such as a patient's breast. A structure 20 is employed to hold the body portion 16 in receiving the radiation beam 14.

The radiation source 12 can be any beam-generating source depending on the nature of treatment or application. By way of example, the radiation source may be a source that generates X-ray beams, proton beams, heavy ion beams such as carbon ion beams, beta ray beams, positron beams, antiproton beams, neutron beams, alpha ray beams, infrared ray beams, visible ray beams, and ultraviolet ray beams, etc. For example, in some embodiments, the radiation source 12 generates X-ray beams at a mega-volt (MV) energy spectrum suitable for treatment of cancer, or X-ray beams at a kilo-volt (kV) energy spectrum suitable for diagnostic imaging of cancer or treatment. Various radiation sources are known to those skilled in the art.

Figure 2:
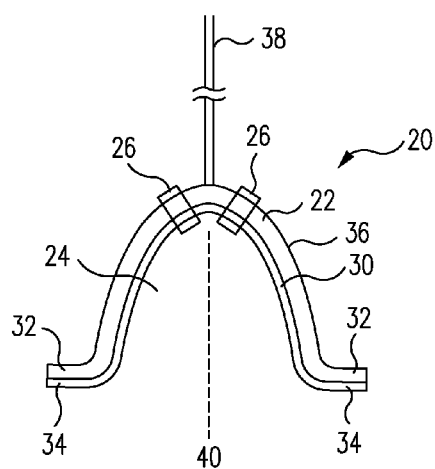
FIG. 2 illustrates a structure that can be used in conjunction with the radiation apparatus illustrated in FIG. 1 in accordance with one embodiment of the invention.
Figure 3:
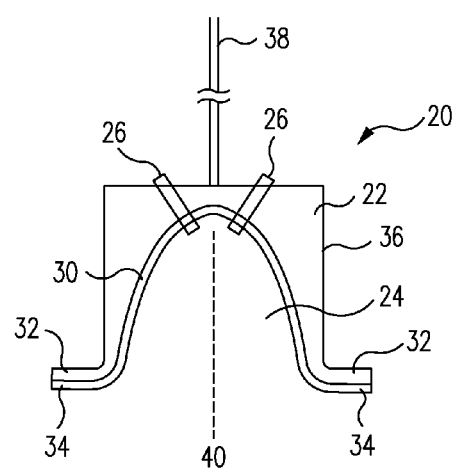
FIG. 3 illustrates a structure that can be used in conjunction with the radiation apparatus illustrated in FIG. 1 in accordance with another embodiment of the invention.

Referring to FIGS. 2-3, the structure 20 in general comprises a member 22 having an interior 24 generally conformal to the shape of the body portion 16. By way of example, the member 22 may be a cup-shaped member that has a generally hemispherical interior 24 conformal to a patient's breast when the breast is uncompressed or pendulous. The member 22 can be custom made matching the size and/or shape of the patient's breast to provide a close fit. One or more small holes or narrow slots 26 may be provided in the wall of the member 22 to connect the interior 24 with a vacuum source 28. This permits the patient 18 to be treated in the supine position yet with the breast 16 supported by the structure 20 so that the breast 16 is generally not compressed by gravity against the patient's rib cage. Instead, the breast 16 may be held in a conformation very similar to the shape it would assume if the patient 18 were prone and the gravity acted to pull the breast 16 away from the chest wall. This increases patient comfort and improve treatment beam access compared to the prone position.

The member 22 is generally rigid. As used herein, the term "rigid" refers to a state of the member that is not pliable by the body portion which is held or supported by the member. A rigid member 22 provides physical support for the body portion 16 in a radiation position. It defines the shape of the body portion 16, immobilizes or stabilizes the body portion 16 under treatment. The member 22 may further function to physically protect the body portion 16 from moving parts such as radiation source 12, etc. In preferred embodiments, the member 22 may perform a combination of several of the above described functions.

The member 22 is preferably made of a material that has a low atomic number, or has a density equal to or lower than that of water. By way of example, the member 22 can be made of beryllium, plastics such as methacrylate plastics, carbon fiber composites, solid foams of various materials, or aerogels. In a preferred embodiment, the member 22 is constructed with more than one layer of suitable materials such as a beryllium outer layer and an aerogel inner layer. Beryllium is a strong, light metal (atomic number of 4). Aerogels are solid-state materials that have highly porous structure and extremely low density. For example, silica nanofoam is the lowest density solid having a density of 1 mg/cm$^3$, as compared to the density of air of 1.2 mg/cm$^3$. An aerogel is derived from a gel in which the liquid component of the gel is replaced with gas. Exemplary aerogels suitable for the material of member 22 include silica gel, alumina gel, and carbon gel. The use of aerogels may reduce skin dose or skin toxicity caused by objects in the beam outside the breast.

In some embodiments, the interior surface of the member 22 can be lined with a thin soft layer 30 to increase comfort to the patient 18. As used herein, the term "soft" refers to being flexible or being easily molded to conform to the shape of the body portion 16. Various suitable materials may be used as the soft liner layer such as silicone foams. Silicone foams are made of polysiloxanes having a silicon-oxygen backbone ( . . . —Si—O—Si—O—Si—O— . . . ). It has ideal properties suitable for pad, gasket, and other products. Open-cell silicone foam is generally of low density or lightweight and allows air and moisture passing through. By way of example, an open-cell silicone foam having e.g., 1-2 mm thickness may be disposed in the interior surface of the member 22.

In some embodiments, inserts of silicone rubber or other soft compressible materials can be used to improve patient's comfort. Inserts of silicone rubber or other soft compressible materials can also be used to compensate for small local changes in breast dimension caused by swelling and inflammation or, conversely, a local contraction during healing.

The member 22 may have a base portion 32 along the periphery of the member 22. The base portion 32 is configured to seal the body portion 16 such as the breast. The base portion 32 may have a flat surface to be against for example the patient's rib cage. Preferably, the base portion 32 is lined with a thin layer 34 such as closed-cell silicone foam to provide a comfortable seal against the skin while enabling light suction to exist within the member interior 24. Closed-cell silicone foam generally does not allow water or air to wick through at low pressures.

The exterior 36 of the member 22 can be in any suitable shape. By way of example, the member 22 may have a hemispherical external shape (FIG. 2) generally matching the interior cavity shape 24 of the member 22. In such embodiments, the member 22 may have an approximately constant wall thickness.

The member 22 may also have an external shape like a cylinder with an approximately hemispherical cavity within it (FIG. 3). In such embodiments, the wall thickness of the member 22 varies. The material or materials made of the member 22 may be chosen to have approximately the same average beam absorption and/or scattering properties as the breast tissue so that the treatment beam 14 transverse the rotation axis 40 of the member 22 passes through an about constant length of materials (breast and member). As such, the effective length of the member-breast material that is traversed by the radiation beam 14 at the nipple end of the breast is about the same as the length that is close to the chest wall. This advantageously aids in treatment planning.

In some embodiments, the structure 20 may include flanges or extensions (not shown) configured to hold or support tissue that extends from the breast towards the axilla or clavicle. The axillary flanges or extension can be an integral portion of the member 22 or may be a separate part removably attached to the member 22. This allows radiation or imaging of the soft tissue between the breast and the axilla. It is advantageous to access both the breast and its axillary extension since primary breast lesions often spread to infect lymph nodes in this region.

In some embodiments, the structure 20 may include one or more markers (not shown) such as radio-opaque marks to aid in e.g. X-ray imaging. Optical markers may also be provided in the structure 20 for a camera to accurately track breathing motion of the patient 18 in real time. This allows compensation of patient's breathing motion by various means during treatment. For instance, the breathing motion can be compensated by controlling the radiation source 12. The radiation source 12 may be controllably turned on or off at specified intervals, thus effectively "freezing" the treatment volume in position. By way of example, SmartTrack/RPM Respiratory Gating System available from Varian Medical Systems, Inc. in Palo Alto, Calif. may be employed in conjunction with the embodiments that include markers.

The structure 20 may include securing members 38 to secure the structure 20 to immobile structures such as to a couch or chair, or to a shield protecting the patient's torso or thorax. The securing member 38 may be connected to a support structure containing springs, gas struts, or similar passive devices, or an active servo system, to maintain a substantially constant supporting force on the securing member 38 and structure 20 while accommodating motion of the patient's chest wall due to breathing.

In use, the structure 20 is placed over a body portion 16 such as a patient's breast. The patient 18 may be supported in any suitable positions including supine, prone, quasi prone, lying side way, seated, standing, and leaning-forward positions. In a preferred embodiment, the structure 20 is advantageously used with patients in a supine position. Once the structure 20 is in place, the air between the breast 16 and the member 22 is drawn by a vacuum source 28 via holes or slots 26 in the member 22. The vacuum source 28 can be any suitable source such as a pump or suction mechanism. The breast 16 becomes expanded upon application of a negative pressure or partial vacuum, and is brought in contact with the interior surface of the member 22. For radiation treatment of a patient breast which has undergone lumpectomy and is still healing, a light suction is proper so long as it is sufficient to bring the breast in contact with the interior surface of the member 22. A soft silicone foam 30 may be used in the interior surface to increase comfort for the patient 18.

Once the patient 18 is secured and properly positioned, imaging and/or radiation therapy can be performed. The structure 20 of the invention supports various imaging and/or treatment options, including computed tomography (CT) or cone beam CT (CBCT), tomosynthesis, intensity-modulated radiation therapy (IMRT), image-guided radiation therapy, arc therapy, and 3-D arc therapy, and so on. These treatment or imaging methods are known to those skilled in the art and therefore they are not described here in detail in order to simply description of the invention.

A structure for holding a portion of a body such as a patient's breast and its use have been described. The structure includes a member having an interior that is generally conformal to a shape of the body portion when pendulous or uncompressed and being provided with one or more openings to be connected to a vacuum source. When in use, the body portion is brought in contact with the interior surface of the member and held in a generally uncompressed shape. The structure can be advantageously used in conjunction with radiation therapy of breast cancer. Of particular advantage, the patient can be supported in a supine position and the breast to be treated is still held in its uncompressed or unconstrained shape. This provides better access for treatment beams, improves patient's comfort, and reduces unnecessary radiation to healthy organs such as heart and lungs. The uncompressed breast and its internal structures supported in the member can be more precisely located with respect to the couch and machine coordinates. The support provided by the structure holds the breast away from the chest wall in a conformation analogous to that of a pendulous breast, however, unlike the case of the prone patient gravity pulls the heart away from the anterior chest wall with the patient supine, thus reducing the exposure of the heart to radiation during treatment. Another advantage is that the support provided by the structure prevents or reduces the formation of re-entrant folds of skin between the breast and the chest wall, which would otherwise be created in the supine treatment position, in which gravity pulls the breast against the chest wall. This is especially the case for women with larger breasts, which tend to spread laterally in the inferior caudal direction and also in the direction away from the contra-lateral breast. The resulting folds of skin are particularly prone to radiation toxicity effects because the plane of the skin within the fold is aligned with the direction of the incident radiation beam. The support provided by the structure of the invention effectively reduces the local radiation dose absorbed by the skin caused by re-entrant folds of the skin.

From the foregoing, it will be appreciated that although specific embodiments of the invention have been described herein for purposes of illustration, various modifications may be made without deviating from the spirit and scope of the invention.

What is claimed is:

1. An apparatus for irradiating a breast of a patient comprising:
   a radiation source;
   a structure adapted to hold a breast of a patient in receiving a radiation from the radiation source, said structure comprising a member having an interior generally conformal to a shape of the patient's breast when uncompressed or pendulous; and
   a vacuum source adapted to provide a negative pressure in the interior of the member, whereby in use of the apparatus with the patient in a supine position the breast is held in the generally uncompressed shape;
   wherein the member is constructed with a material or materials that has or have an average radiation beam absorption and/or scattering property substantially same as that of the breast.

2. The apparatus of claim 1 wherein the member has a generally hemispherical interior and exterior, thereby a substantially constant wall thickness.

3. The apparatus of claim 1 wherein the member has a generally hemispherical interior and a generally cylindrical exterior, thereby a substantially different wall thickness.

4. The apparatus of claim 1 wherein the member is generally rigid.

5. The apparatus of claim 1 wherein the member is constructed with materials comprising an aerogel.

6. The apparatus of claim 1 wherein the structure further comprises an extension coupled to a periphery of the member adapted to hold tissue between the breast and axilla.

7. The apparatus of claim 1 wherein the structure further comprises one or more markers adapted to track motions of the breast.

8. The apparatus of claim 1 further comprising a securing member coupled to the structure adapted to provide a substantially constant supporting force to the structure.

9. The apparatus of claim 8 wherein the securing member is movable to accommodate motions of the breast.

10. A structure for holding a portion of a body, comprising a member having an interior that is generally conformal to a shape of the body portion when pendulous or uncompressed, said member being provided with one or more openings to be connected to a vacuum source which is adapted to provide a negative pressure to the interior, whereby when in use of the structure, the body portion is held in the generally uncompressed shape, wherein the member is constructed with a material or materials that has or have an average radiation beam absorption and/or scattering property substantially same as that of the body portion.

11. The structure of claim 10 wherein the member has a generally hemispherical interior and exterior, thereby a substantially constant wall thickness.

12. The structure of claim 10 wherein the member has a generally hemispherical interior and a generally cylindrical exterior, thereby a substantially different wall thickness.

13. The structure of claim 11 wherein the member is generally rigid.

14. The structure of claim 10 further comprising a layer of a generally soft material lining the member interior.

15. The structure of claim 10 wherein the member further comprises one or more markers adapted to track motions of the body portion.

16. The structure of claim 10 wherein the member is adapted to hold a breast of a patient in a supine position.

17. The structure of claim 10 wherein the member is adapted to hold a breast of a patient in a supine position and the structure further comprises an extension coupled to a periphery of the member adapted to hold tissue between the breast and axilla.

18. The structure of claim 10 wherein the member is constructed with materials comprising an aerogel.

19. The structure of claim 10 further comprising a securing member coupled to the member adapted to provide a substantially constant supporting force to the member.

20. The apparatus of claim 19 wherein the securing member is movable to accommodate motions of the body portion.

21. A method of irradiating a breast of a patient, comprising the steps of:
    placing a breast of a patient in a structure, said structure comprising a member having an interior generally conformal to a shape of the patient's breast when pendulous or uncompressed;
    positioning the patient in a supine position;
    applying a negative pressure in the interior, thereby bringing the breast in contact with the member in the generally uncompressed shape; and
    delivering a radiation beam to at least a portion of the breast.

22. The method of claim 21 wherein said radiation beam is X-ray beam.

23. The method of claim 21 wherein said radiation beam is X-ray beam at a mega-volt level.

24. The method of claim 21 further comprising the step of moving the structure in the delivering step to accommodate motions of the breast.

* * * * *